United States Patent [19]

Vickers

[11] 4,434,177
[45] Feb. 28, 1984

[54] α-METHYLDOPA-L-ASCORBIC ACID COMPOSITIONS

[75] Inventor: Stanley Vickers, Perkasie, Pa.

[73] Assignee: Merck & Co., Inc., Rahway, N.J.

[21] Appl. No.: 315,696

[22] Filed: Oct. 28, 1981

Related U.S. Application Data

[62] Division of Ser. No. 139,913, Apr. 14, 1980, Pat. No. 4,321,264.

[51] Int. Cl.$^3$ ............................................. A61K 31/375
[52] U.S. Cl. ..................................................... 424/280
[58] Field of Search ......................................... 424/280

[56] References Cited

U.S. PATENT DOCUMENTS 3,344,023  9/1967  Reinhold et al. ................... 424/319

Primary Examiner—Richard A. Schwartz
Attorney, Agent, or Firm—Alice O. Robertson; Daniel T. Szura

[57] ABSTRACT

The application discloses a pharmaceutical composition for treating hypertension containing (A) L-α-methyl-3,4-dihydroxyphenylalanine and (B) salicylamide, phenylglyoxal or L-ascorbic acid.

7 Claims, No Drawings

α-METHYLDOPA-L-ASCORBIC ACID COMPOSITIONS

This is a division of application Ser. No. 139,913, filed Apr. 14, 1980 now U.S. Pat. No. 4,321,264.

BACKGROUND OF THE INVENTION

The present invention concerns a pharmaceutical composition for treating hypertension. The components are L-α-methyl-3,4-dihydroxyphenylanine and salicylamide phenylglyoxal or L-ascorbic acid.

L-α-methyl-3,4-dihydroxyphenylalanine (α-methyldopa) is a commercial antihypertensive agent [see Merck Index 9th Ed., Item 5925 (1976)]. Salicylamide is a commercial analgesic [Merck Index 9th Ed., Item 8080 (1976)]. Phenylglyoxal apparently has no commercial pharmaceutical utility. L-ascorbic acid is a vitamin.

The combination of methyldopa with salicylamide phenylglyoxal or L-ascorbic acid has been found to have enhanced antihypertensive properties.

SUMMARY OF THE INVENTION

A pharmaceutical composition for treating hypertension containing (A) α-methyldopa and (B) salicylamide, phenylglyoxal or L-ascorbic acid and a method of treatment.

DESCRIPTION OF THE PREFERRED EMBODIMENT

An embodiment of the present invention is a pharmaceutical composition for treating hypertension containing (A) L-α-methyl-3,4-dihydroxyphenylalanine (α-methyldopa) and (B) salicylamide, phenylglyoxal, or L-ascorbic acid wherein the weight ratio of (A):(B) is at least about 3:1.

The (A):(B) weight ratio in the composition of the present invention may be varied. A preferred weight ratio of (A):(B) is about 16:1 to about 3:1. A more preferred (A):(B) weight ratio is about 12:1 to about 3:1. A still more preferred weight ratio is about 8:1 to about 4:1.

One preferred embodiment of the present inventive composition is one containing α-methyldopa and phenylglyoxal. More preferred embodiments of this composition contain weight ratios as set out above.

Another preferred embodiment of the present inventive composition is one containing α-methyldopa and L-ascorbic acid. More preferred embodiments of this combination have weight ratios as set out above.

Still another preferred embodiment of the present inventive composition is one containing α-methyldopa and salicylamide. More preferred embodiments of this combination have weight ratios as recited above.

The compositions of the present invention may be administered either orally or parenterally in treating hypertension in humans. Appropriate dosage forms are used. Oral administration is preferred. Suitable oral dosage forms may be solid e.g. tablets, troches, capsules and the like, or liquid e.g. solution, suspension, emulsion and the like. Where necessary, or desirable, common pharmaceutically acceptable compounding ingredients i.e. diluents, carriers, processing acids, etc. may be used in preparing the dosage forms. Conventional procedures, compounding ingredients and equipment are used to prepare the oral and/or parenteral dosage forms.

The weight ratio of the (A) and (B) components in the dosage form will be within the ranges already set out above.

In treating hypertension in humans, an antihypertensive effective amount of the composition containing the (A) and (B) components is administered. The daily dosage of the composition will be varied depending on various factors e.g. the severity of the hypertension (high blood pressure), the weight of the patient etc. Generally, daily dosages may range up to about 3000 mg, preferably from about 250 mg to about 2000 mg, and more preferably from about 500 mg to about 1500 mg.

The enhanced effectiveness of the present composition as an antihypertensive agent was demonstrated in an in vivo test using spontaneously hypertensive (SH) rats. The representative combination tested contained α-methyldopa and salicylamide. The data for this in vivo test is tabulated below:

TABLE 1

ANTIHYPERTENSIVE ACTIVITY IN SH RAT ORAL ADMINISTRATION

| Test No. | Composition Containing | Dose (mg/kg) | No. of Rats | Mean Arterial Pressure[1] (mm/Hg) Hours After Treatment | | | | | | | |
|---|---|---|---|---|---|---|---|---|---|---|---|
| | | | | 0 | ½ | 1 | 2 | 4 | 8 | 12 | 18 |
| 1 | α-Methyldopa | 80 | 10 | 164 | 155 | 164 | 148 | 141 | 152 | 158 | 160 |
| 2 | α-Methyldopa | 80 | 16 | 173 | 178 | 172 | 163 | 152 | 154 | 166 | 169 |
| 3 | α-Methyldopa + Salicylamide | 80 + 10 | 5 | 174 | 162 | 161 | 153 | 142 | 136 | 150 | 148 |
| 4 | α-Methyldopa + Salicylamide | 80 + 20 | 3 | 186 | 172 | 170 | 167 | 154 | 170 | 168 | 176 |
| 5 | α-Methyldopa + Salicylamide | 80 + 40 | 2 | 164 | 144 | 158 | 156 | 158 | 160 | 158 | 160 |

[1] Average

The data shows that the combination of α-methyldopa and salicylamide, weight ratio 8:1 and 4:1, is more effective than α-methyldopa in reducing mean arterial pressure of SH rats. This indicates that the compositions of the present invention would be more effective than α-methyldopa in treating hypertensive humans.

Claims to the invention follow.

What is claimed is:

1. A pharmaceutical composition for treating hypertension wherein the antihypertensively effective component consists essentially of (A) L-α-methyl-3,4-dihydroxyphenylalanine and (B) L-ascorbic acid wherein the weight ratio of (A):(B) is at least about 3:1.

2. The pharmaceutical composition of claim 1 wherein the weight ratio of L-α-methyl-3,4-dihydroxyphenylalanine:L-ascorbic acid is about 3:1 to about 16:1.

3. The pharmaceutical composition of claim 2 wherein said ratio is about 4:1 to about 8:1.

4. The pharmaceutical composition of claim 3 wherein said ratio is 4:1.

5. The pharmaceutical composition of claim 3 wherein said ratio is 8:1.

6. A method of treating hypertension in humans by administering a anti-hypertensive effective amount of a claim 1 composition.

7. The method of claim 6 wherein the composition is administered orally.